US00PP29052P2

(12) United States Plant Patent
Olesen

(10) Patent No.: US PP29,052 P2
(45) Date of Patent: Mar. 6, 2018

(54) *CLEMATIS* PLANT NAMED 'EVIPO078'

(50) Latin Name: *Clematis viticella*
Varietal Denomination: Evipo078

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/330,281

(22) Filed: Sep. 6, 2016

(51) Int. Cl.
*A01H 5/02* (2006.01)

(52) U.S. Cl.
USPC ..... Plt./228

(58) Field of Classification Search
USPC ..... Plt./228
CPC ..... A01H 5/02
See application file for complete search history.

(56) References Cited

PUBLICATIONS http://floradania.dk/en/nyheder/new-varieties/new-variety/art/clematis-hybrida-x-acropolistm-boulevardr-evipo078n/; Jan. 22, 2016; 2 pages.*

* cited by examiner

*Primary Examiner* — Kent L Bell

(57) ABSTRACT

A new *Clematis* plant with a compact growth habit, profuse, pink flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification:
Genus: *Clematis.*
Species: *viticella.*
Variety denomination: 'Evipo078'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2005 and the resulting seeds were planted the following winter in a controlled environment in Guernsey, Channel Islands, United Kingdom. The new variety named 'Evipo078' originated as a single seedling from the stated cross.

The new *clematis* plant may be distinguished from its female seed parent and male pollen parent by the following characteristics. The female seed parent has red tepals while the new variety has pink tepals. The male seed parent has light pink tepals while the new variety has pink tepals.

The objective of the hybridization of this *clematis* plant was to create a new and distinct variety for nursery culture with unique qualities such as:

1. Uniform and abundant pink flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo078' was selected by Mogens N. Olesen and Raymond J. Evison in their *clematis* development program in the Channel Islands, United Kingdom in 2006. Asexual reproduction of 'Evipo078' by means of vegetative cuttings and traditional layering was first performed by Mogens N. Olesen and Raymond J. Evison in the nursery during the summer of 2006. This initial and subsequent asexual propagations have demonstrated that the characteristics of 'Evipo078' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo078'.

Specifically illustrated in FIG. 1 of the drawings is an open flower above view, tepals detached showing reproductive flower parts, and a cluster of flower buds and open flower from the branch.

Figure 1:
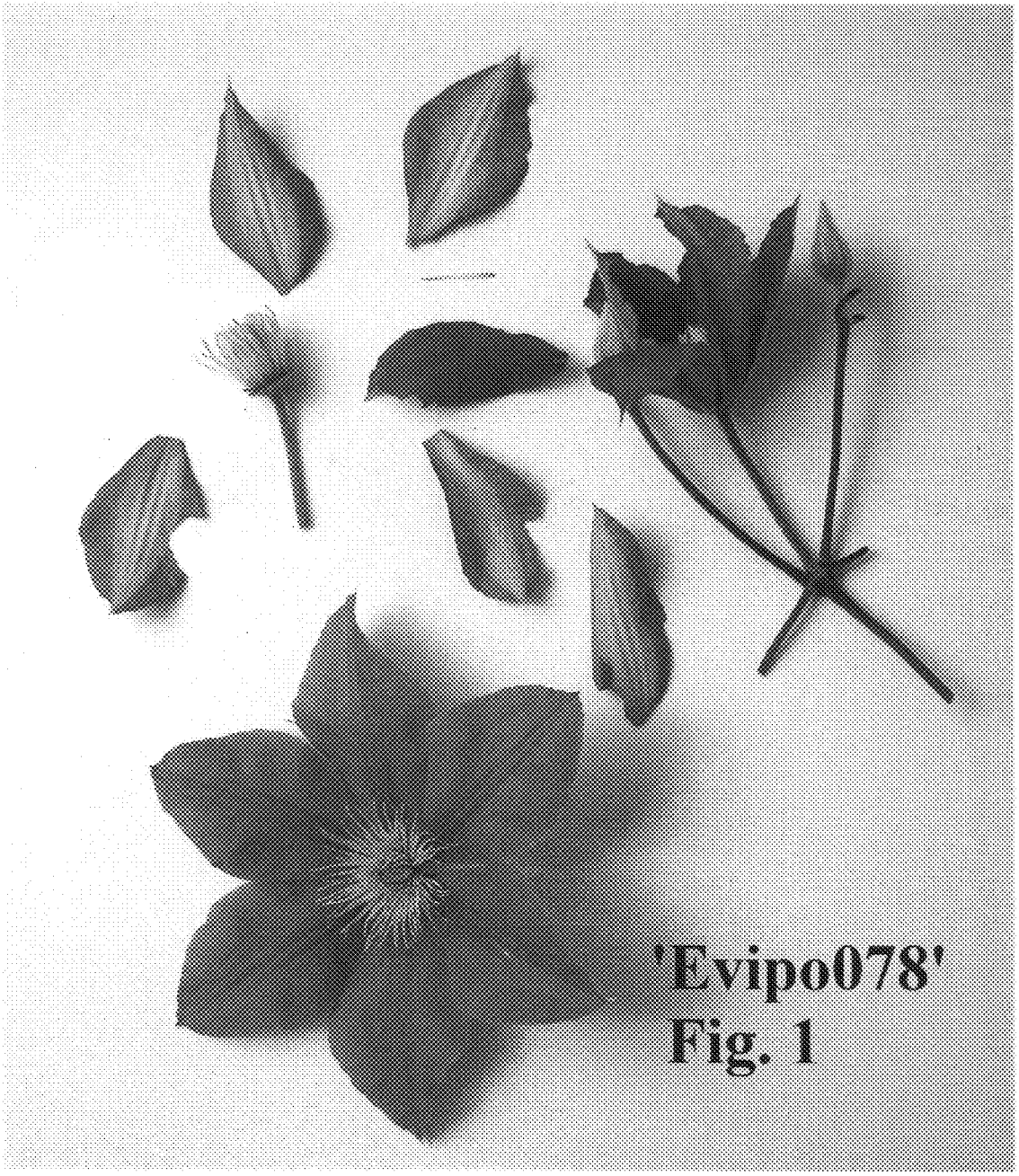
Figure 2:
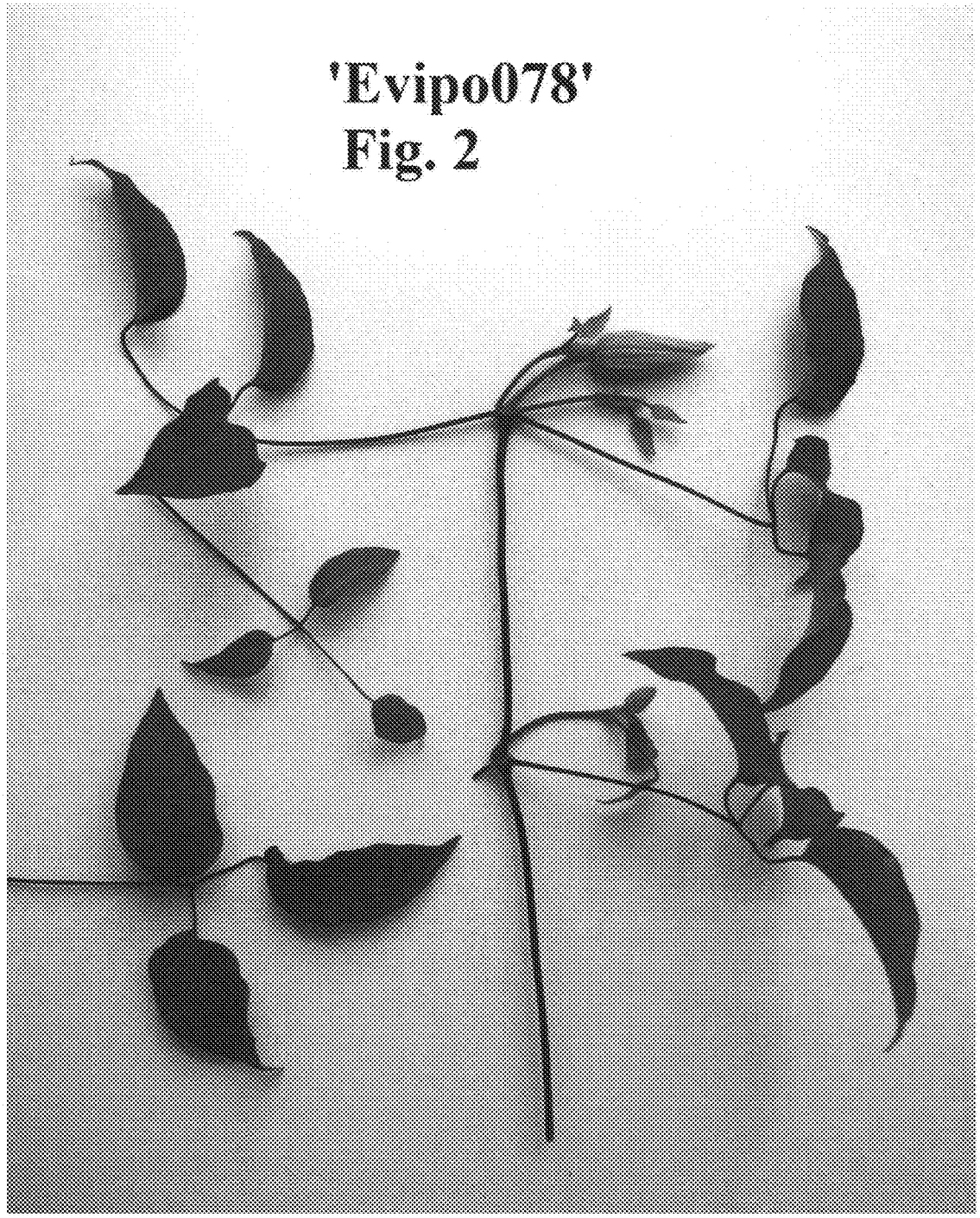

Specifically illustrated in FIG. 2 are leaves attached to the stem and flower bud. Plants shown are 2 years of age.

DETAILED DESCRIPTION OF THE VARIETY

The following is a detailed description of 'Evipo078', as observed in its growth throughout the flowering period in Marion County Oreg. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo018' described and illustrated in U.S. Plant Pat. No. 16,267 are compared to 'Evipo078' in Chart 1.

CHART 1

| | ''Evipo078' | 'Evipo018' |
|---|---|---|
| Flower diameter | 130 mm | 80 to 90 mm |
| Tepal upper surface upon opening | Red-Purple Group 67A | Red-Purple Group 71A |
| Tepal count | 6 | 6 |

FLOWER AND FLOWER BUD

Blooming habit: Recurrent. The natural flowering period is generally from May to September.

Flower bud:

*Size*.—Normally 35 mm in length. Bud diameter is 15 mm.

*Bud form*.—Elliptic, broad at the base.

*Bud color*.—At ¼ opening Yellow-Green Group 145B.

*Texture*.—Highly pubescent.

Pedicel:

*Surface texture*.—Pubescent.

*Length*.—On average 20 mm in length with 2 mm diameter.

*Color*.—Yellow-Green Group 145B.

*Strength*.—Moderately strong.

Receptacle:

*Surface texture*.—Lightly pubescent.

*Shape*.—Broad funnel.

*Size*.—2 mm (h)×2 mm (w).

*Color*.—Yellow-Green Group 145B.

Flower arrangement:

*Location on vine*.—New and old growth.

*Borne*.—Normally in clusters of 3 flowers on terminal and axillary buds.

Flower bloom:

*Size*.—On average, flowers are 130 mm in diameter and 20 mm in depth.

*Profile*.—Open flowers are flat.

*Fragrance*.—None.

*Lasting quality*.—Flowers normally remain up to 10 days on the plant.

Tepals:

*Tepal color*.—Upon opening, the upper surface is Red-Purple Group 67A. The lower surface is Purple Group N78C at margins, Violet Group 85B intermediate, with a central bar Green White Group 157A. After opening, tepal coloration remains the same on both upper and lower surfaces.

*Quantity*.—Normally 6 tepals.

*Size*.—55 mm in length by 30 mm wide.

*Shape*.—Individual tepal shape is elliptic. The tepal apex is acute. The tepal base is acute.

*Apex recurvature*.—Slightly recurved.

*Tepal cross section*.—Flat.

*Margins*.—Entire. Weak undulations of margin observed.

*Persistence*.—Tepals drop off cleanly.

Reproductive organs:

*Arrangement*.—Open.

*Pollen*.—None observed.

*Anthers*.—Size: 6 mm in length. Color: Yellow Group 3C. Quantity: On average, 40.

*Filaments*.—Color: Yellow Group 4D. Length: 5 mm.

*Pistils*.—Quantity: On average, 20.

*Stigmas*.—Level in location relative to the length of the filaments and the height of the anthers.

*Styles*.—Color: Green White 157A. Length: 12 mm.

PLANT

Plant form: Climbing.

Plant growth: Moderately vigorous.

Size: Seasons growth attains 100 cm in height. Average spread is 50 cm.

Stems:

*Color*.—Juvenile stems are Yellow-Green Group 144A. Mature stems are Greyed-Purple Group 183A.

*Internodes*.—On average, 10 cm between nodes.

*Length*.—Normally 45 cm from the base of the plant to the flowering portion of the stem.

*Diameter*.—Normally 3 mm.

*Texture*.—Mature stems are ribbed.

Plant foliage:

*Leaf characteristics*.—Deciduous.

*Arrangement*.—Trifoliate.

*Leaf size*.—Terminal leaflets are normally 55 mm (l)× 35 mm (w). Entire leaves are 130 mm (l)×90 mm (w).

*Abundance*.—On average 2 leaves per 10 cm of stem.

*Leaf color*.—Juvenile upper Yellow-Green Group 144A with Greyed-Purple Group 183B at the margins. Juvenile lower Yellow-Green Group 144A. Mature upper Yellow-Green Group 146A. Mature lower Yellow-Green Group 146A.

*Stipules*.—Absent.

*Petioles*.—Size: Normally 80 mm in length by 2 mm diameter. Texture: Pubescent. Color: Greyed-Purple Group 183A.

*Petioloule*.—Size: Normally 20 to 40 mm in length by 2 mm diameter. Texture: Pubescent. Color: Greyed-Purple Group 187A.

*Leaflet shape*.—Generally ovate. The base is rounded. The apex is acute.

*Margin*.—Entire.

*Surface*.—The upper side is smooth. The lower side is smooth.

*Thickness*.—Moderate.

*Glossiness*.—Moderately glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo078', substantially as described and illustrated, due to its abundant pink flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo078'

'Evipo078'